United States Patent [19]

Martin

[11] Patent Number: 5,797,910
[45] Date of Patent: Aug. 25, 1998

[54] OPERATIVE EQUIPMENT FOR CORRECTING A SPINAL DEFORMITY

[75] Inventor: Jean-Raymond Martin, Tournefeuille, France

[73] Assignee: Paulette Fairant, Tournefeuille, France

[21] Appl. No.: 605,038

[22] PCT Filed: Aug. 23, 1994

[86] PCT No.: PCT/FR94/01021

§ 371 Date: Feb. 27, 1996

§ 102(e) Date: Feb. 27, 1996

[87] PCT Pub. No.: WO95/05786

PCT Pub. Date: Mar. 2, 1995

[30] Foreign Application Priority Data

Aug. 27, 1993 [FR] France .................................. 93 10291
Feb. 7, 1994 [FR] France .................................. 94 01440
Jul. 15, 1994 [FR] France .................................. 94 08794

[51] Int. Cl.$^6$ ................................................. A61B 17/70
[52] U.S. Cl. ........................... 606/61; 606/54; 606/59
[58] Field of Search .......................... 606/60, 61, 54, 606/59

[56] References Cited

U.S. PATENT DOCUMENTS

| | | |
|---|---|---|
| 3,865,105 | 2/1975 | Lode . |
| 3,977,397 | 8/1976 | Kalnberz et al. . |
| 4,078,559 | 3/1978 | Nissinen . |
| 4,112,935 | 9/1978 | Latypov . |
| 4,271,836 | 6/1981 | Bacal et al. . |
| 4,289,123 | 9/1981 | Dunn . |
| 4,386,603 | 6/1983 | Mayfield . |
| 4,445,513 | 5/1984 | Ulrich et al. . |
| 4,448,191 | 5/1984 | Rodnyansky et al. . |
| 4,505,268 | 3/1985 | Sgandurra . |
| 4,611,582 | 9/1986 | Duff . |
| 4,836,196 | 6/1989 | Park et al. . |
| 4,854,496 | 8/1989 | Bugle . |
| 4,946,458 | 8/1990 | Harms et al. . |
| 5,219,349 | 6/1993 | Krag et al. . |
| 5,281,223 | 1/1994 | Ray . |

FOREIGN PATENT DOCUMENTS

| | | |
|---|---|---|
| 0140790 | 5/1985 | European Pat. Off. . |
| 0260044 | 3/1988 | European Pat. Off. . |
| 0418387 | 3/1991 | European Pat. Off. . |
| 0499037 | 8/1992 | European Pat. Off. . |
| 0470660 | 12/1992 | European Pat. Off. . |
| 1397395 | 3/1965 | France . |
| 2689750 | 10/1992 | France . |
| 2697744 | 5/1994 | France . |
| 2845647 | 8/1980 | Germany . |
| 3807346 | 6/1989 | Germany . |
| 848009 | 8/1979 | U.S.S.R. . |
| 888968 | 11/1979 | U.S.S.R. . |
| 780652 | 8/1957 | United Kingdom . |
| 2162065 | 1/1986 | United Kingdom . |
| 2198647 | 6/1988 | United Kingdom . |
| 8504096 | 9/1985 | WIPO . |
| 9213496 | 8/1992 | WIPO . |

*Primary Examiner*—Michael Buiz
*Assistant Examiner*—Daphna Shai
*Attorney, Agent, or Firm*—Harold H. Dutton, Jr.

[57] ABSTRACT

Ancillary equipment for subjecting a portion of the spine to sustained stress in order to correct and/or maintain the shape of and/or the forces exerted on the vertebrae before and during the positioning of spinal implants. The equipment includes at least two engagement ends (6a, 6b, 6c, ... and/or 6a', 6b', 6c', ... ) for engaging one or preferably both sides of at least two separate respective vertebrae, while at the same time engaging the parallel longitudinal rails (3) of a frame-like support (1) via corresponding corrective branches (4a, 4b, 4c, ... and/or 4a', 4b', 4c', ... ) and a removable base (5) of said engagement ends, and further includes members (13, 17, 43, 65) for adjusting and locking the engagement ends (6a, 6b, 6c, ... and/or 6a', 6b', 6c', ... ) in their relative positions in each or a combination of three orthogonal directions.

21 Claims, 7 Drawing Sheets fig. 1 fig. 2 fig. 3 fig. 4 fig. 5 fig.6 fig. 7

OPERATIVE EQUIPMENT FOR CORRECTING A SPINAL DEFORMITY

The invention concerns operative equipment for correcting a spinal deformity prior to the installation of implanted spinal instrumentation such as an osteosynthetic device, an intervertebral device for treating instabilities or a corrective dynamic implanted orthosis, or other such.

BACKGROUND OF THE INVENTION

Spinal osteosynthetic devices are already known for treating scoliotic deformities, consisting of components for anchoring to the vertebrae, such as hooks or intrapedicular screws, and rods or frames fixed to the anchoring components to impose a relative position on the different vertebrae. These rigid, semi-rigid or semi-flexible osteosynthetic devices rigidify the spinal column in the corrected position and are more often associated with an intervertebral arthrodesis with or without a bone graft.

These known osteosynthetic devices still present many problems as regards the installation and stability of the anchoring components, and the attachment of rods, plates or frames to the anchoring components, which must be carried out simultaneously to reduce deformity.

Thus, reducing deformity by installing an osteosynthetic device still presents problems. In point of fact, it must be possible to produce this reduction in deformity at the same time as, and by the attachment of, vertebral instrumentation, and this in three dimensions. In particular, with a scoliosis, it is advisable not only to reposition the vertebrae in the same sagittal plane, but also to re-establish the kyphosis and/or the lordosis while carrying out a derotation of the vertebrae. Osteosynthetic devices of the Cotrel-Dubousset type enable this problem to be partially resolved. They consist of two posterior bilateral rods, arched during the operation, immediately before their attachment to the anchoring components, in relation to the lateral deviation, then turned through 90° to place their curvature in a sagittal plane in order to re-establish the kyphosis or lordosis and to carry out a derotation of the vertebrae, at least partially. The correction is limited by the fact that it is carried out only by the rod of the concavity which is first turned and then attached to the anchoring components: it thus stabilizes the correction obtained but it practically annuls any corrective potential of the rod of the convexity which only has a stabilizing effect through its insertion and attachment. The two rods are then connected together by transverse tensioning rods stabilizing the assembly in the position obtained. Even if the curvature of the rods can be adjusted, after their insertion, by the lever arms, the latter can ensure the desired kyphosis or lordosis but they do not allow satisfactory derotation of the vertebrae to be achieved.

Other types of osteosynthetic devices are employed for treating spinal deformities and use sub-laminar wires connected to rods (Luque) or to frames (Dove) or connect plates or rods while engaging the vertebrae by means of hooks and/or intrapedicular screws. Apart from the risk of neurological complications presented by these systems through the entry of equipment into the canal, their potential for correcting vertebral deformities remains limited and incomplete.

Moreover, it is also desirable to have available operative equipment suitable for installing new dynamic orthoses which preserve the physiological mobility of the vertebrae and comprise means for elastic return which has to be installed extended, and has the characteristics that must be determined prior to this installation to ensure that the resulting correction is maintained, and to permit movements in the instrumented vertebral zone.

Known operative equipment consisting of single clamps with two articulated arms and exerting forces of distraction or compression, does not resolve the various problems associated with total correction of spinal deformities.

Kluger has described operative equipment for the correction of vertebral collapse (traumatic or tumoral) by supporting the two adjacent vertebrae, the separation of which is achieved by a distraction-compression device: the height of the vertebrae under consideration is thus reconstituted. This equipment cannot enable a spinal deviation to be corrected, given that it is only applied to two vertebrae which it can only bring closer together or separate. It maintains the position obtained until connecting equipment is inserted which will finally fix the vertebrae in this position.

In addition, Bookwalter has described a spinal frame which serves to support the paravertebral muscles with separators. its aim and effect is only to separate the paravertebral muscles to improve exposure of the vertebrae during surgery: in no case does this equipment act on the vertebrae themselves.

Bulky external equipment is also known for reducing vertebral deformities consisting of harnesses and/or rings and/or belts associated with distraction devices (motors, weights, etc). This equipment is not very precise, is not flexible in use, and does not enable a large correction of the positions of the vertebrae to be made precisely in three dimensions.

Thus, no known operative equipment enables the positions of the vertebrae to be controlled with precision in three dimensions in space in the frontal, sagittal and horizontal planes.

The invention thus aims at overcoming these disadvantages and providing operative equipment for correcting and/or maintaining, with great precision and in three dimensions, the shape and/or the forces exerted between the vertebrae before and during the installation of implanted spinal instrumentation.

The invention also aims at providing operative equipment for installing a dynamic implanted vertebral orthosis. In particular, the invention also aims at providing operative equipment for measuring the movements and forces necessary to maintain the correction and which will thus be incorporated in the installed osteosynthetic or dynamic orthosis instrumentation.

The object of the invention is also to provide operative equipment which is simple in its structure and use and takes up little room in the operating area.

DESCRIPTION OF THE INVENTION

In order to do this, the invention concerns operative equipment for exerting and maintaining constraints on a portion of the spinal column with a view to correcting and/or maintaining the shape and/or the forces exerted on the vertebrae before and during the fixing of implanted spinal instrumentation, comprising a rectangular frame intended to surround the vertebral region to be instrumented and formed of two upper and lower short transverse sides, and of four longitudinal parallel bars, two on each side of the spinal column, on which corrective arms slide.

According to the invention, these corrective arms comprise a base which enables each arm to be attached transversely to the two longitudinal bars of the frame while preserving complete freedom of movement and ability to slide longitudinally. The corrective part of each arm, the end of which is intended to engage the corresponding side of the chosen vertebra, rests on the base. This end will ensure movement of the instrumented vertebral side in a frontal and/or sagittal direction under the respective action of two handles operating screw threads situated on spindles pressing on the base. The movements thus made are evaluated by metric scales whereas the forces are measured by the corresponding dynamometers.

According to the invention, the forces of distraction and/or compression which come into play in the correction of vertebral deformities are evaluated by measuring devices which are either a dynamometric clamp with two arms or a dynamometric distraction device of the sliding calliper type, each of these acting on the base of the corrective arms. Each corrective arm is independent on the same side of the frame and is indirectly connected, via the vertebra with which it is engaged, to the corrective arm situated, on the same vertebra, on the opposite side of the spinal column. Thus each vertebra chosen to be instrumented is subjected, on each of its right and left sides, to different actions from two corrective arms situated respectively on the right and left of the frame.

The invention also concerns operative equipment comprising in combination all or part of the characteristics referred to above or hereinafter.

DESCRIPTION OF THE DRAWINGS

Other characteristics and advantages of the invention will become apparent on reading the following detailed description which refers to the annexed drawings in which.

DETAILED DESCRIPTION OF THE PREFERRED EMBODIMENTS

In all the text, and unless stated to the contrary, the term "vertical" designates the axial direction of the spinal column which does not always correspond to the absolute vertical direction since the column has curvatures in kyphosis and/or lordosis. Similarly, the term "horizontal" designates any direction contained within the plane perpendicular to the vertical direction, the term "sagittal" designates any plane containing the antero-posterior vertical and horizontal directions, and the term "frontal" designates any plane containing the lateral vertical and horizontal directions. These terms are thus used with reference to each vertebra and not, in an absolute sense, with reference to the patient.

Figure 1:
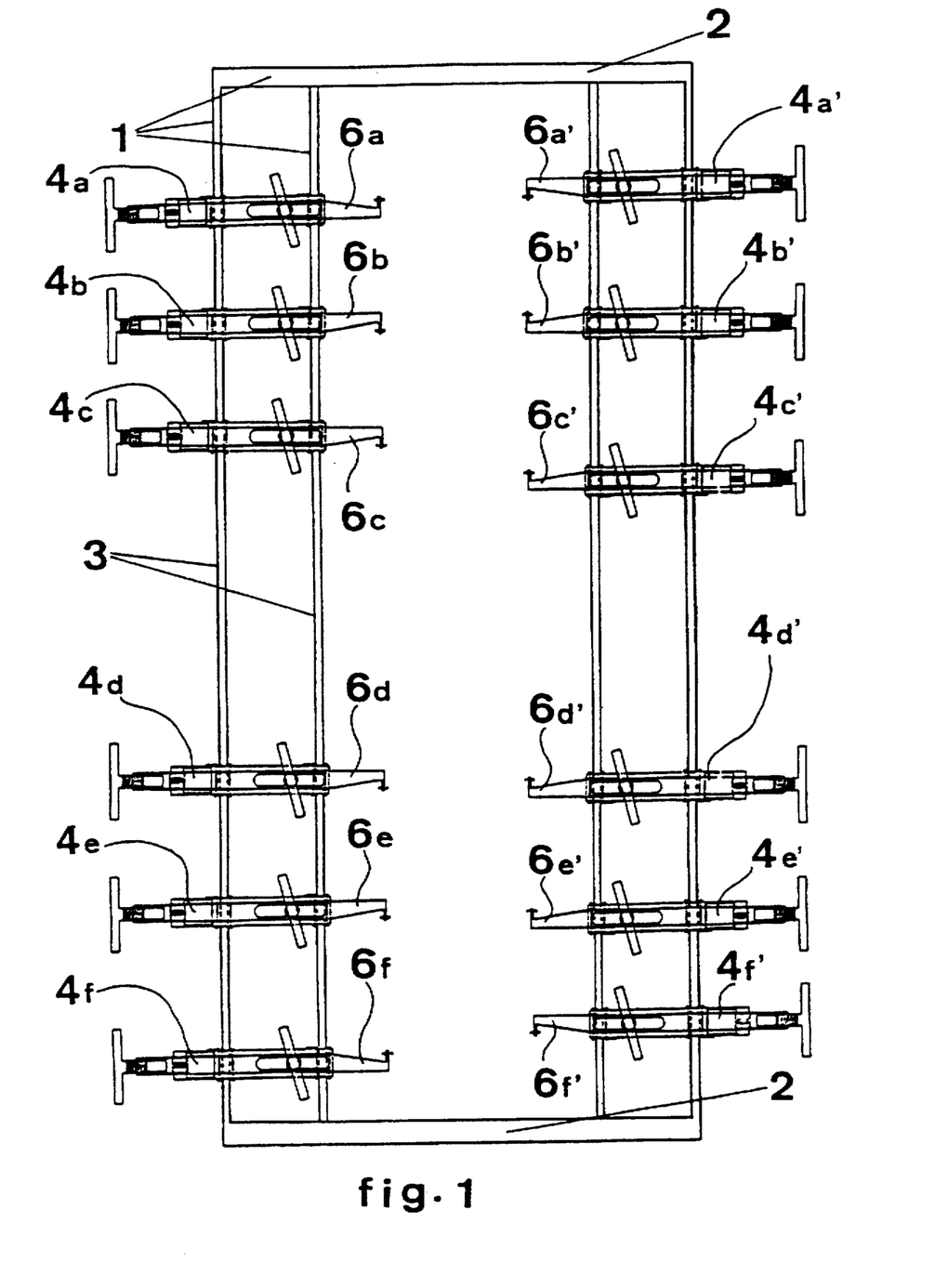
FIG. 1 is a diagrammatic rear view of an operative frame with several vertebral corrective arms.

FIG. 1 represents an operative frame according to the invention for correcting in particular a spinal deformity of the scoliotic type and/or the hyper-kyphotic type and/or the hyper-lordotic type. This rectangular frame (1) has:

two short transverse sides (2) positioned at the upper and lower part of the spinal column. These short sides are a priori fixed but may possibly be telescopic so that their length can be adjusted to the distance between the long sides.

two long longitudinal sides (3) consisting of two parallel bars, on either side of the spinal column, on which the bases (5) of the corrective arms (4) slide. The distance between the two long sides (3) is fixed symmetrically and corresponds to that of the attachment cylinders (8) of the bases (5) of the corrective arms (4): it is of the order of 10 to 15 cm. The length of the longitudinal sides (3) should be greater than that of the instrumented column and justifies the availability of two or more frame lengths so as to be able to use the one suited to the size of the subject and to the height (number of levels) of the column to be corrected.

According to the invention, this frame is attached by its sides and/or by its ends (preferably at the corners) to the operating table or to the support on which the patient lies in ventral decubitus. This attachment is made by means of articulated arms (on average two to four) which are locked to immobilize the frame once the latter has been positioned with respect to the patient. The articulated arms are attached to the frame by means of self-locking clamps.

Figure 2:
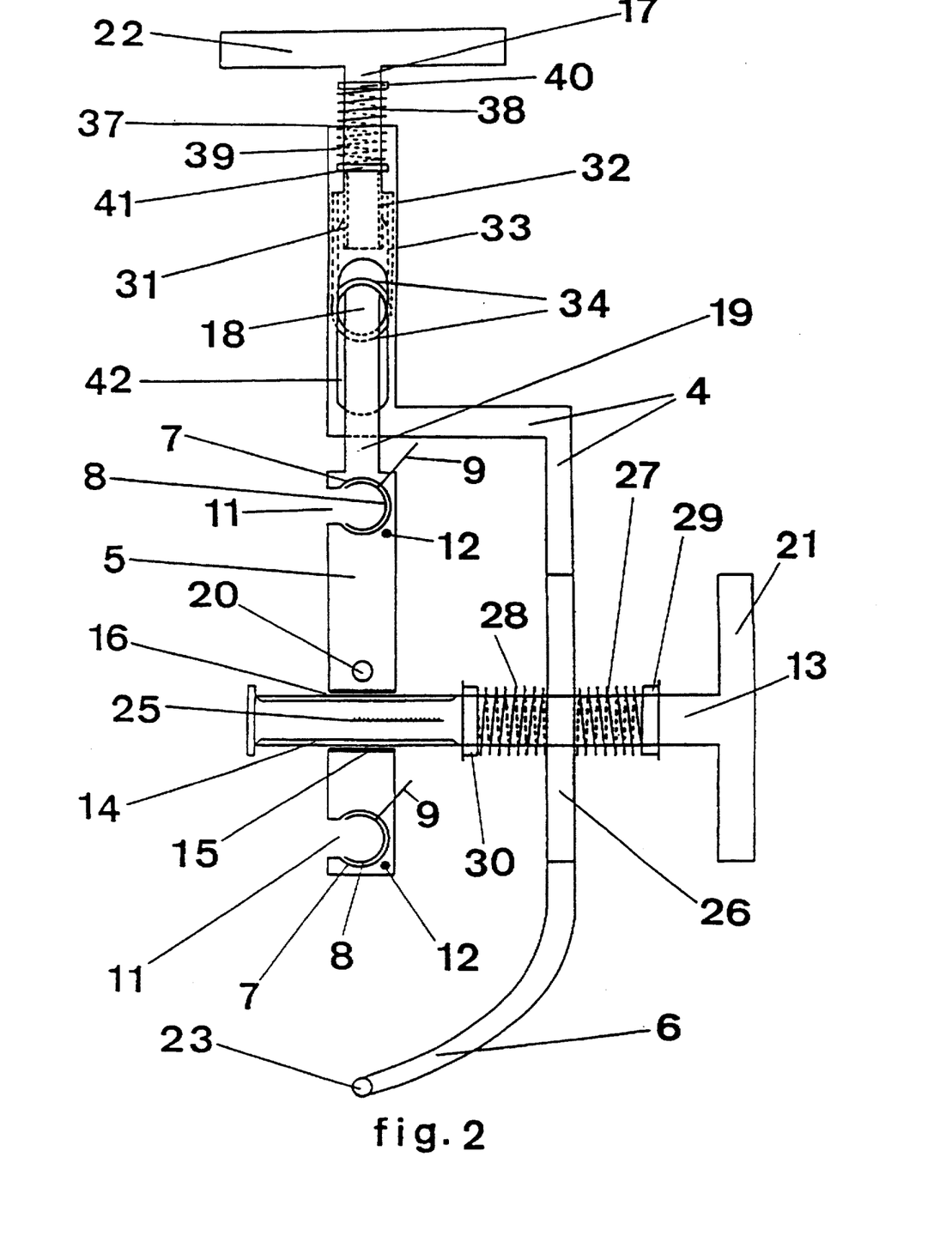
FIG. 2 is a diagrammatic view in lateral section along the axis III—III of a corrective dynamometric arm of the frame.
Figure 3:
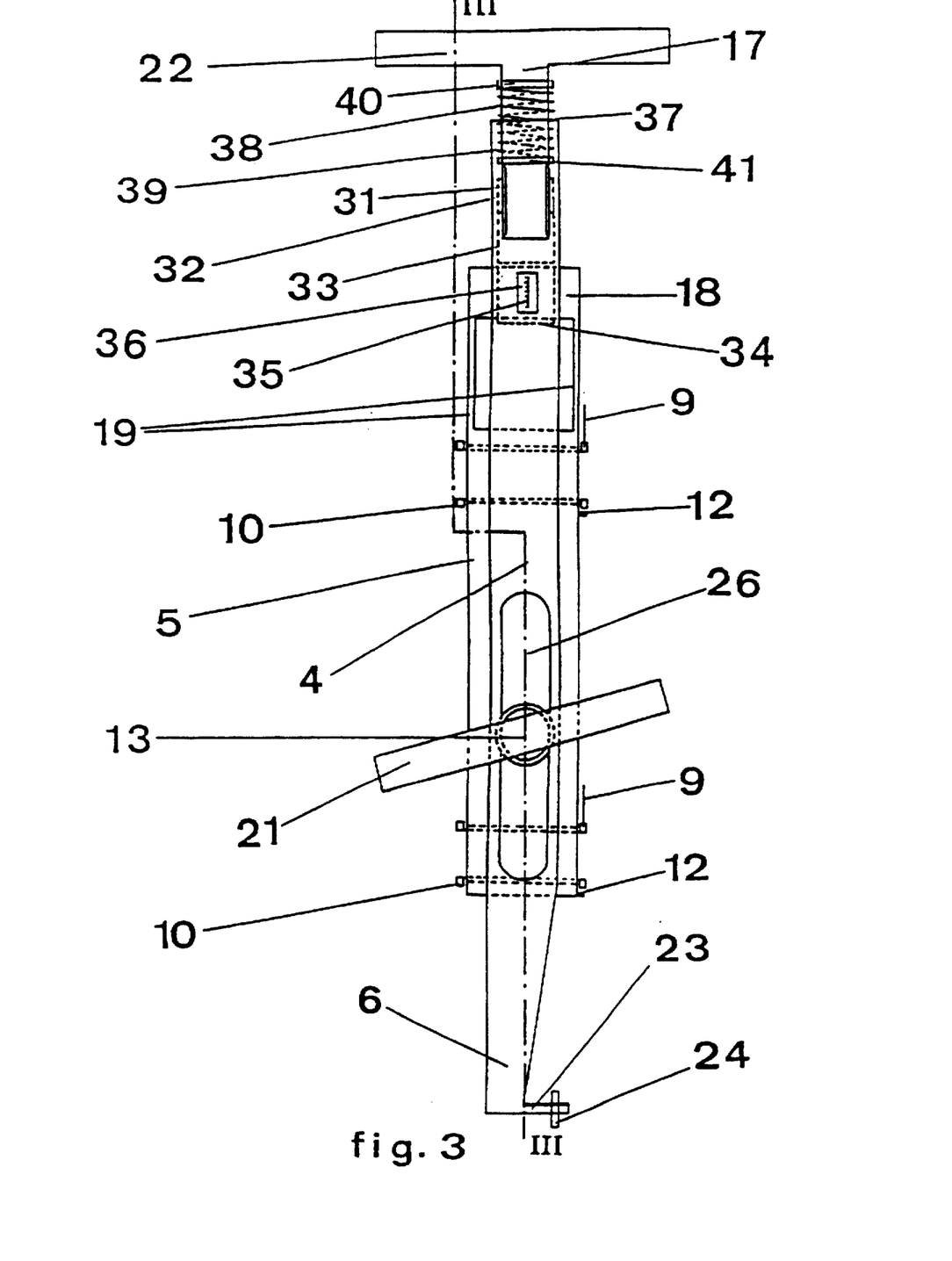
FIG. 3 is a diagrammatic view from above of a corrective dynamometric arm of the frame.

FIGS. 2 and 3 show the corrective arms, according to the invention, which consist of two parts: a first lower part (5) or base, the purpose of which is on the one hand to attach the arm to the frame while allowing free longitudinal movements and on the other hand to engage the second so-called "corrective" part (4). This corrective part (4) is attached at its free end (6) to the anchoring component, such as a hook plate (and hence to the vertebra) to act by means of two distinct handles (21, 22).

Advantageously, according to the invention, the corrective arms do not form an integral part of the frame: they are removable and thus can be added to or taken away according to requirements. A corrective arm corresponds to one side of an instrumented vertebra.

According to the invention, the arms (4) are attached by their base (5) to the two parallel rods (3) of the frame either side of the column by two cylindrical recesses (7) provided at their lower part. Each cylindrical recess (7) encloses another concentric cylinder (8), free to rotate axially, but not free to move longitudinally, which turns inside the first one (7) by action exerted on an outer handle (9). Longitudinal translation of the internal cylinder (8) is limited by a peripheral swelling (10) on this cylinder at each of its ends and on the outside of the main cylinder (7) of the base. The transverse handle (9) which enables rotation to take place rests on this external swelling (10) of the cylinder (8).

These two cylinders (7 and 8) are open (11) longitudinally at their lower part to allow entry of each corresponding longitudinal rod (3) of the frame. The width of this opening (11) is just greater than the diameter of the longitudinal rod (3) of the frame which will be inserted in it. Similarly the internal diameter of the cylinder (8) is just greater than that of the bar (3) which will hold it without gripping it. Locking is then achieved by rotating the central cylinder (8) which thus closes the lower window (11). The base (5) of the corrective arm (4) thus can no longer leave the two parallel rods (3) of the frame but is free to make longitudinal sliding movements on these along a vertical axis. A pin (12) situated on the side of the base (5) enables the handle (9) to be locked in the "closed" position of the central cylinder (8).

According to the invention, the horizontal sagittal rod (13) of the corrective arm (6) moves perpendicularly to its base (5) through which it passes while rotating. It moves by means of a thread (14) which corresponds to an internal thread (15) provided in the corresponding horizontal sagittal hole (16) of the base (5).

According to the invention, the horizontal frontal rod (17) of corrective arm (4) moves while pressing on a frontal vertical spindle (18) of the base (5), situated in its horizontal extension. This spindle (18) is supported and attached at each of its ends by two parallel extensions (19) of the base (5) which enable the corrective arm (4) to move in a horizontal frontal direction as they separate.

According to the invention, the measuring devices in distraction-compression are supported on the lateral faces situated in the horizontal plane of the base (5), at the level of the blind holes (20) so that the lugs (44, 49) of the measuring devices in distraction-compression can enter. These holes are situated halfway between the two attachment cylinders (8) to the two parallel longitudinal rods (3) of the frame: the action of the measuring devices in distraction-compression is made in a balanced manner on the base which moves vertically in the frontal plane on the two longitudinal rods (3) of the frame.

According to the invention, the corrective arm properly so-called (4) moves horizontally in the sagittal plane and in the frontal plane under the action of the two spindles (13, 17) pressing on the base (5), and moved by the two handles (21, 22). It is fixed, for example by a pin (23) at its dynamic end (6), on the upper or lower face of the means for anchoring the instrumented vertebra. This pin (23) has a screw (24) at its end which stabilizes the "anchoring component-corrective arm" connection. This pin (23) can be used when a hook plate is employed as a means of anchoring the instrumented vertebra, and any other means of attachment (hook, clamp, fork, etc) can be used at this dynamic end (6) of the corrective arm (4) to press on the vertebra in relation to the anchorage of the implanted vertebral system.

According to the invention, the horizontal sagittal movement of the pin (23) of the dynamic end (6) of the corrective arm (4) is made by means of a sagittal rod (13) provided, at its end, with a thread (14) engaged in an internal thread (15) of the base (5). The position of the corrective arm (4) in relation to the base (5) is indexed by a graduated scale (25) on the rod (13) or by electronic means not shown. This corrective arm (4) has an oblong slot (26) through which the horizontal sagittal control rod (13) passes. This oblong slot (26) extends in a direction at right angles to the vertical direction passing through the longitudinal rails (3) of the frame and the axis of the sagittal rod (13). Thus it is possible to move this corrective arm (4) in relation to the sagittal horizontal axis. The oblong slot (26) of this corrective arm (4) is held captive between two springs (27, 28) the opposite ends of which press on the dynamometric sensors (29, 30) carried by the sagittal horizontal rod (13). These dynamometric sensors (29, 30) provide a measurement of the forces imparted to the dog (23) of the dynamic end (6) of the corrective arm (4) in the horizontal sagittal direction. By turning the handle (21) of this sagittal rod (13) the position of the corrective arm (4) is adjusted in the sagittal-horizontal direction in relation to the frontal plane containing the longitudinal rails (3) of the frame (1).

According to the invention, the horizontal frontal movement of the pin (23) of the free end (6) of the corrective arm (4) is ensured by a frontal control rod (17) which enables movements of this corrective arm (4) to be made in the frontal-horizontal direction perpendicular to the vertical direction passing through the longitudinal rails (3) of the frame (1). This frontal control rod (17) has a threaded end (31) engaged in an internal thread (32) provided in a bearing (33) comprising a cylinder (34) surrounding the vertical spindle (18) situated in the extension of the base (5) and attached to this by two parallel extensions (19). The cylinder (34) has a graduated scale (35) visible through a slot (36) in the corrective arm (4) which enables the movement of this arm (4) to be evaluated. The end (37) of this arm (4) opposite the dog (23) slides about the frontal control rod (17) and is held captive about two springs (38, 39), the opposite ends of which press on the dynamometric sensors (40, 41) carried by the frontal rod (17). These springs and these sensors thus form an axial stop in two directions for the end (37) of this corrective arm (4) in relation to the frontal control rod (17). Movement of the corrective arm (4) in the horizontal frontal direction in relation to the sagittal control rod (13) is permitted by an oblong slot (26). The vertical spindle (18) of the base (5) passes through the corrective arm (4) through an oblong slot (42) provided axially in this arm to permit relative movements in the horizontal frontal direction. By turning the handle (22) of the frontal rod (17) the position of the dog (23) of the dynamic end (6) of the arm (4) is thus adjusted in the frontal plane.

The corrective force applied to the vertebra corresponds to a tension on the concavity and a thrust on the convexity and results in each case in compression of one of the two longitudinal springs (38 or 39) situated on the frontal control rod, the compressive force being evaluated by the corresponding dynamometric sensor (40 or 41) which transmits data directly to the computer.

Figure 4:
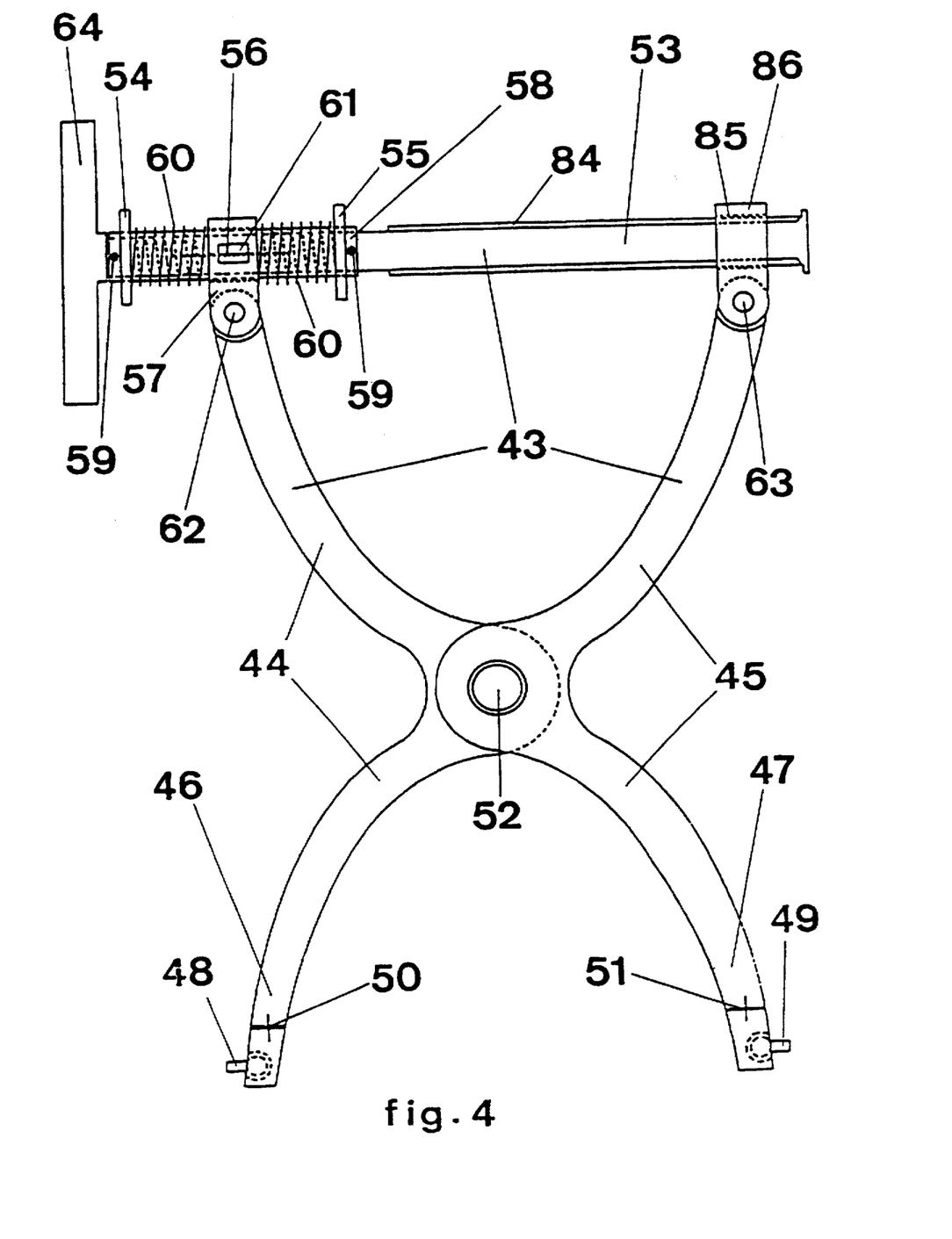
FIG. 4 is a diagrammatic side view of a dynamometric clamp, a device for measuring the forces in distraction and/or in compression.
Figure 5:
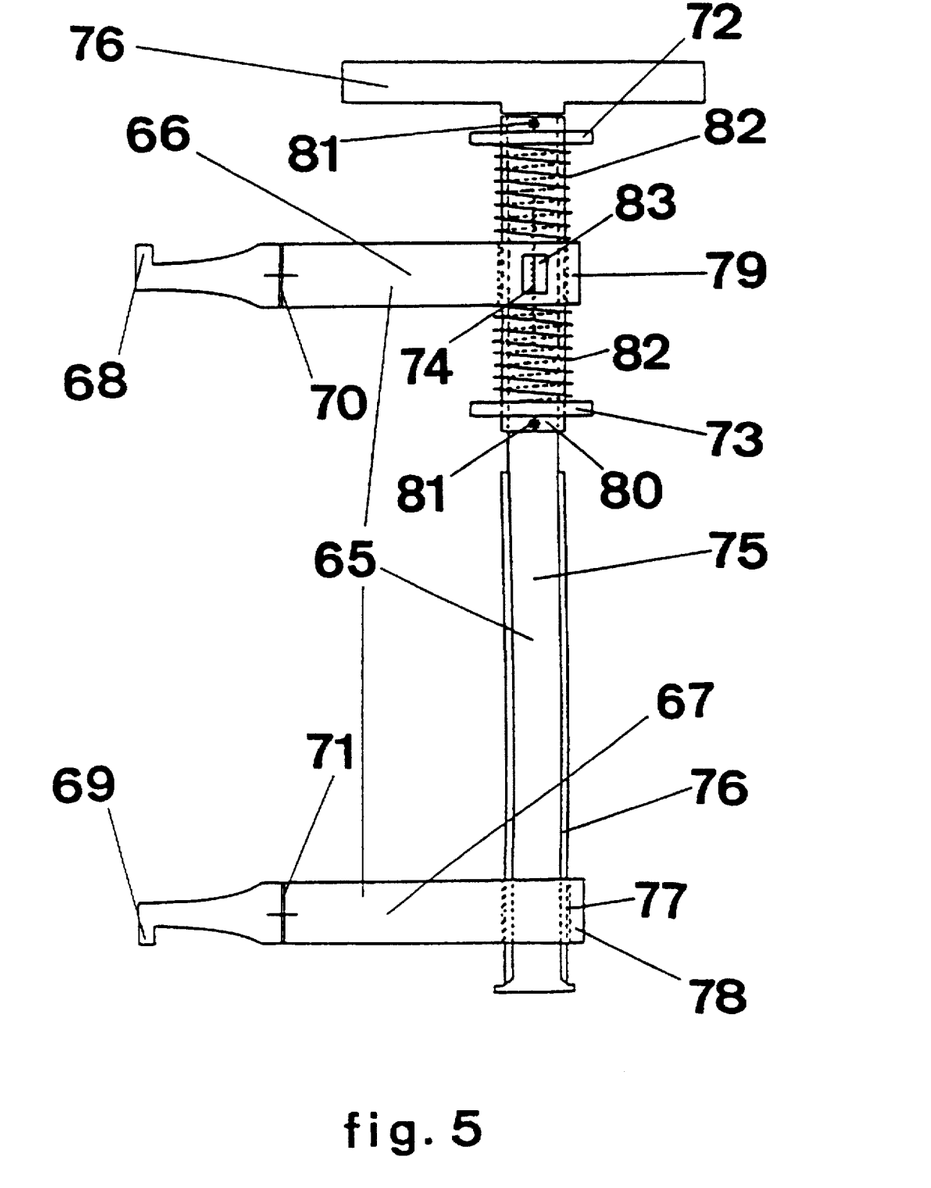
FIG. 5 is a diagrammatic side view of a dynamometric device for measuring the forces in distraction and/or in compression.

FIGS. 4 and 5 show, according to the invention, the measuring devices (43, 65) in distraction-compression which will not cause any movement since complete correction in the three planes is obtained by the arms (4) of the frame (1). These components enable the forces to be measured in distraction or in compression which are required of the springs of a dynamic orthosis. These springs are interposed between the vertebrae and press on the means of anchorage. The forces produced by these springs will thus reduce by the same amount those required of the connecting rods; a reduction in the diameter of connecting rods thus accentuates the residual flexibility of the system. These distraction-compression forces are "resting forces" since they do not cause any movement of the arms to which they are applied.

This measurement is thus made in the frontal plane and in the vertical direction of the two longitudinal parallel rods (3) of the frame (1).

These components (43, 65) in addition enable the distance to be measured between two non-adjacent instrumented vertebrae, a measurement which corresponds to the chord of the arc of curvature in kyphosis-lordosis chosen for the vertebral zone considered.

FIG. 4 shows, according to the invention, an operative clamp (43) which comprises two operational ends (46 and 47) intended to engage the bases (5) of the corrective arms (4) of the frame (1). Each of the operational ends (46 and 47) of the clamp (43) is formed of a dog (48, 49) intended to be engaged in the hole (20) of the base (5) of the corrective arm (4), in order to act in compression or in distraction on this base (5), mid-way between the two parallel bars (3) of the frame (1). To do this, each dog (48, 49) may be directed upwards or downwards by rotating it about its axis (50, 51).

According to the invention, the clamp also comprises dynamometric means (54 and 55) for measuring the forces exerted on the end dogs (48, 49) to maintain their relative positions. The clamp also has metric or electronic means (56) for measuring movements of the end dogs (48, 49) during adjustments to their relative positions.

Each clamp consists of two arms (44, 45), carrying dogs (48, 49) at their free end, which are articulated to each other about a horizontal axis (52) at right angles to the direction passing through the two dogs (48, 49). The two arms (44, 45) are controlled in their relative movements by a control rod (53) provided with a manipulating handle (64).

A control rod (53) has a thread (84) engaging an internal thread (85) of a sleeve-shaped end (86) of the arm (44) opposite the dog (49). The end (57) of the arm (44) opposite the dog (48) is in the form of a sleeve sliding about a cylinder (58) fixed to the vertical control rod (53) but the position in translation in relation to this rod (53) can be adjusted by means of locking screws (59), making it possible to adjust the distance between the dogs (48, 49) in the rest position. This sleeve (57) is held captive between two compression springs (60) pressing at their opposite ends on the dynamometric sensors (54, 55) carried by the cylinder (58) and hence by the vertical control rod (53). The springs (60) and their sensors (54, 55) thus form an axial stop in two directions for the end (57) of the arm (44) in relation to the control rod (53). The sleeve (57) also comprises a slot (61) making it possible to read a graduated scale (56) engraved on the rod (53). The sleeves (86, 57) of the ends of the arms (45, 44) engaging the vertical control rod (53) are articulated to these arms (45, 44) about an axis (63, 62) parallel to the axis (52) of articulation of the arms (44, 45) between them. When the handle (64) is turned, the end dogs (48, 49) are separated or brought closer together. If the dogs (48, 49) do not bear any forces in the vertical direction, the sleeve (57) remains mid-way between the two sensors (54, 55), the springs (60) not being activated. If on the contrary a force is necessary to move the dogs (48, 49), one of the springs (60) is activated in compression to balance this force and to permit the position to be adjusted. One of the sensors (54, 55) then delivers an electric signal proportional to this force.

FIG. 5 shows, according to the invention, an operative sliding calliper (65) for measuring distraction-compression forces, which comprises two operational ends (66 and 67) intended to engage the bases (5) of the corrective arms (4) on the frame (1). Each of the operational ends (66 and 67) of the sliding calliper (65) is formed of a dog (68, 69) intended to be engaged in the hole (20) of the base (5) of the corrective arm (4), so as to act in compression or in distraction on this base (5), half-way between the two parallel bars (3) of the frame (1). In order to do this, each dog (68, 69) can be directed upwards or downwards by rotating it about its axis (70, 71).

According to the invention, the sliding calliper (65) has dynamometric means (72, 73) for measuring the forces exerted on the end dogs (68, 69) to maintain their relative positions. The sliding calliper (65) also has means (74) for measuring movements of the end dogs (68, 69) when their relative positions are adjusted.

Each sliding calliper (65) consists of two arms (66, 67) carrying dogs (68, 69) at their free ends which remain parallel in their movements which are controlled by an orthogonal control rod (75) provided with a manipulating handle (76).

A control rod (75) has a thread (76) engaging an internal thread (77) of a sleeve-shaped end (78) of the arm (67) opposite the dog (69). The end (79) of the arm (66) opposite the dog (68) is in the form of a sleeve sliding about a cylinder (80) fixed to the vertical control rod (75) but whose position in translation, in relation to this rod (75), can be adjusted by means of locking screws (81), making it possible to adjust the distance between the dogs (68, 69) in the rest position. This sleeve (79) is held captive between two compression springs (82) pressing at their opposite ends on the dynamometric sensors (72, 73) carried by the cylinder (80) and hence by the vertical control rod (75). The springs (82) and their sensors (72, 73) thus form an axial stop in two directions for the end (79) of the arm (66) in relation to the control rod (75). Movements of the sleeve (79) are evaluated, either by reading, through a slot (83), a graduated metric scale (74) engraved on the rod (75), or by an electronic device not shown. When the handle (76) is turned, the end dogs (68, 69) are separated or brought closer together. If the dogs (68, 69) do not bear any forces in the vertical direction, the sleeve (79) remains mid-way between the two sensors (72, 73), the springs (82) not being activated. If on the contrary a force is necessary to move the dogs (68, 69), one of the springs (82) is activated in compression to balance this force and to permit the position to be adjusted. One of the sensors (72, 73) then delivers an electric signal proportional to this force.

These two components (43 and 65) for measurements in distraction-compression enable the action of the corrective arms (4) fixed to the frame (1) to be supplemented. They reduce the horizontal, sagittal or frontal transverse forces on these arms and make it possible to measure the forces required in distraction or in compression of the springs of a dynamic internal vertebral orthosis which will be placed between the anchoring components.

Figure 6:
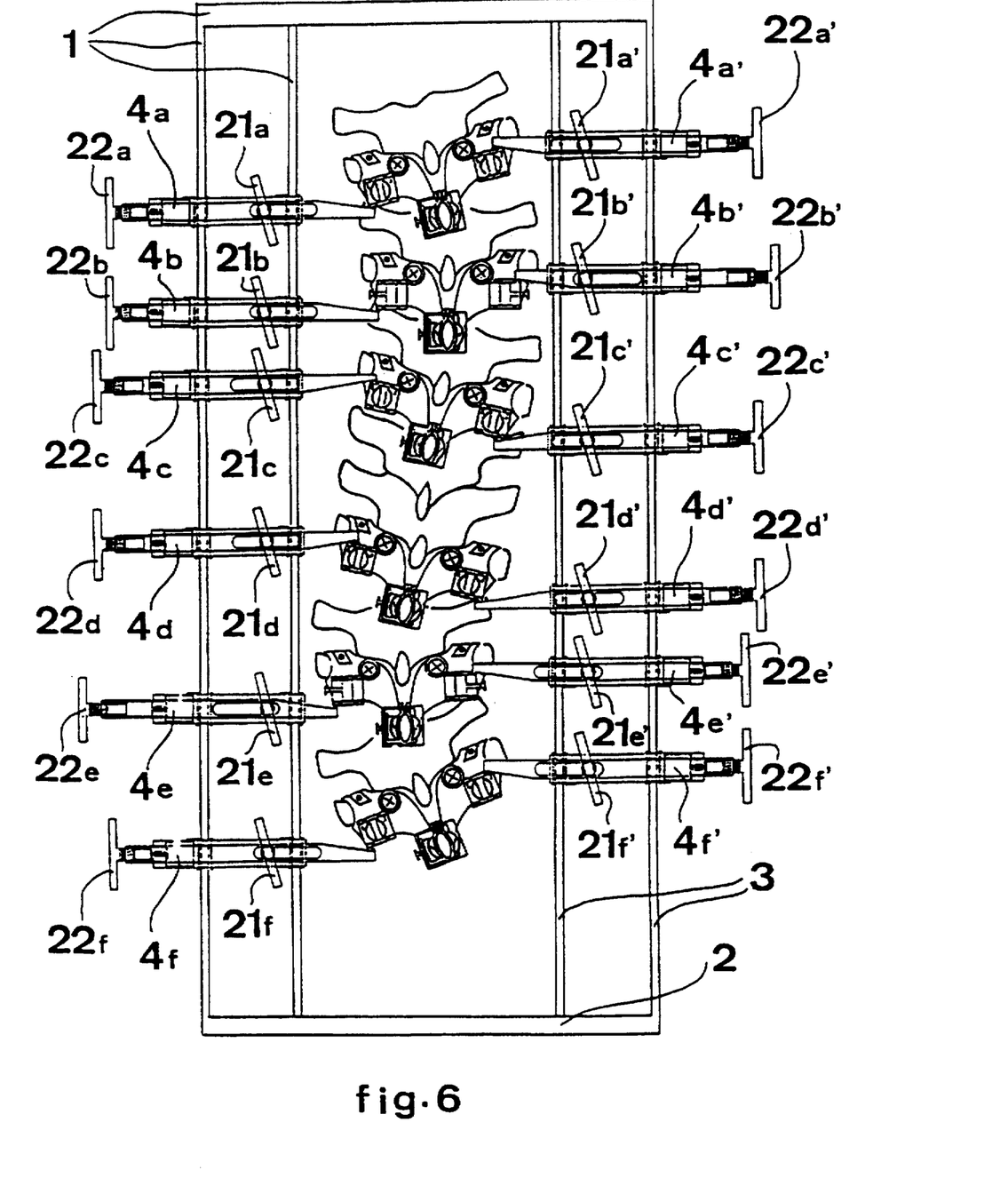
FIGS. 6 and 7 are views of phases in the correction of a vertebral deformity of the scoliotic type and of the insertion of a dynamic internal vertebral orthosis with the aim of maintaining this correction while permitting a certain vertebral mobility.
Figure 7:
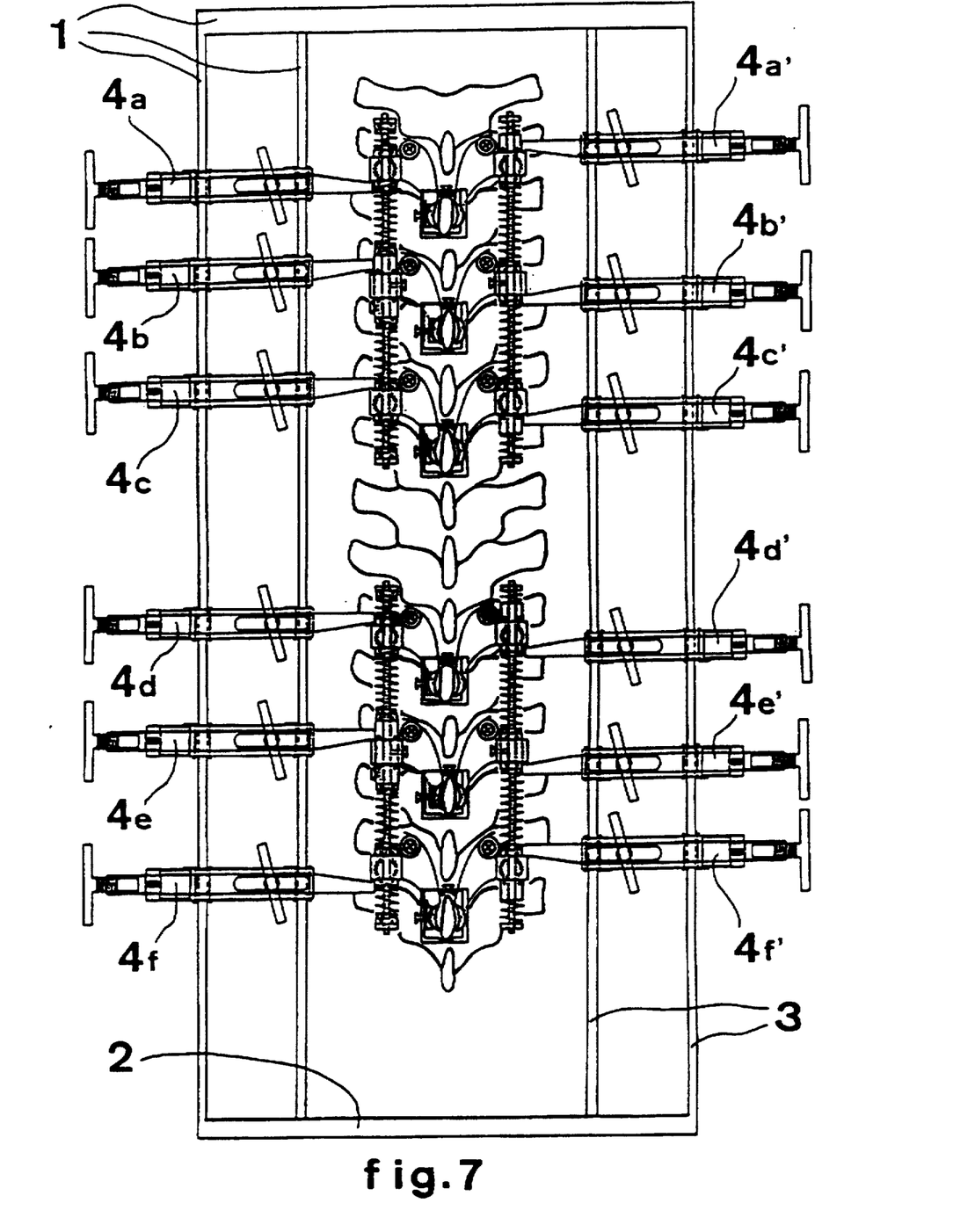

FIGS. 6 and 7 show a process for using operative equipment, according to the invention, for the correction of a spinal deformity of the scoliotic type and maintenance of this correction by the insertion of a dynamic internal vertebral orthosis.

The patient is positioned in ventral decubitus on conventional thoracic and pelvic supports and a posterior median approach is made over the length of the zone to be instrumented. After disengagement of the paravertebral muscular masses, the anchoring equipment is attached to the chosen vertebrae in order to carry out either an osteosynthesis or to install a dynamic vertebral orthosis.

This anchoring equipment should comprise an attachment zone for the corrective ends of the arms of the frame which are to be fixed there. The anchorage equipment is usually bilateral but if correction is to be applied to a minimal deviation it may be placed unilaterally.

The frame (1) is then positioned with its two parallel, bilateral longitudinal bars (3) either side of the operating zone. The length of the frame is chosen so that the two short upper and lower transverse sides (2) are placed beyond the upper and lower ends of the incision.

Sterile articulated arms, attached either to the operating table or to the patient's support, enable the frame (1) to be firmly fixed in space. The longitudinal rails should not be in contact with the posterior wall of the patient, whether at the thoracic level or at the level of the buttocks so as to allow free movement of the bases (5) of the corrective arms (4) on these rails (3).

Each base (5a, 5b, 5c etc on the left or 5a', 5b', 5c' etc on the right) of the corrective arm (4a, 4b 4c etc on the left or 4a', 4b', 4c' etc on the right) is placed on the two longitudinal rails (3) of the frame (1) opposite each vertebra and then locked by rotating the corresponding cylinders (8) of the base (5). Two corrective arms (4), one on each side, are positioned on the same instrumented vertebra by means of bilateral anchorage and possibly on one side (usually that of the concavity) in the case of a small unilaterally instrumented deviation.

By rotating the handles (21, 22) respectively of the sagittal-horizontal rods (13) and frontal-horizontal rods (17), the dynamic ends (6) of each corrective arm (4) are positioned in contact with the means of anchorage where they are attached by a screw (24) on the dog (23) as in the case of a dynamic orthosis. FIG. 6 shows the system in equilibrium and in the resting position before any correction.

Correction is made in a progressive manner by rotating the sagittal-horizontal rods (13) and frontal-horizontal rods (17):

The frontal-horizontal rods (17) should be rotated by their handles (22) simultaneously on either side of the instrumented vertebra. In point of fact, the distance between the two means of fixing the dynamic ends (6) of the corrective arms (4) is constant on the vertebra. Each corrective arm (4) thus moves symmetrically and an equilibrium results between the distraction forces of the concavity and the compressive forces on the convexity of the curvature. If in the convexity, the compressive force recorded by the dynamometer (40) is low in relation to that of the concavity recorded by the dynamometer (41), or even more if we record a tensile force in the convexity, this means that the thrust of the corrective arm (4) in the convexity is not sufficient compared with the tension exerted by the corrective arm (4) of the concavity.

The system is considered to be in equilibrium, whether or not total correction is obtained in relation to mechanical spinal problems or problems of neurological pain, when the tensile forces of the concavity and the compressive forces of the convexity are identical or have very similar values.

Rotation of the sagittal-horizontal rods (13) by their handles (21) is not made symmetrically as with the frontal-horizontal rods (17).

Each frontal-horizontal rod (17) undergoes a double movement either side of the instrumented vertebra in two planes:

sagittal, in kyphosis or lordosis horizontal, for correcting curvature in the frontal plane.
As the position of the vertebra to be corrected is not symmetrical in relation to its centre in these two planes, each side of this instrumented vertebra will not be subjected to the same movement during correction: in the concavity, there is a larger movement, as far as the desired corrected position, than on the side of the convexity. In fact it is the correction of kypho-lordosis symmetrically between the concavity and the convexity which will enable total derotation of the vertebra to be achieved, associated with correction of the curvature in the frontal plane.

Movement in the sagittal and horizontal plane of each side of the spine thus brings about a total correction of the vertebral rotation by a bilateral action which creates a derotating effect. The desire kyphosis or lordosis position is obtained in a precise manner by calculating the deviation from the desired curvature, reproduced between the central corrective arm and (and hence of the top of the curvature) and the two corrective arms positioned on the adjacent vertebrae. The desired kypho-lordosis Cobb angle α, determined prior to the operation, makes it possible to calculate the deviation in curvature knowing the chord of the arc (distance between the extreme vertebrae given by the measuring devices (43, 65), according to the formula:

$$\text{Deviation} = \tan\frac{\alpha}{4} \times \frac{\text{chord}}{2}.$$

The total correction having been obtained, we have the forces necessary for this correction, which are given us on each clamp by the two dynamometers (29, 30, 40, 41). The reduction in the forces required on the connecting rods will make it possible to reduce the diameter of the latter and hence their rigidity, thus preserving their maximum flexibility so as to facilitate freedom of movement of the spinal column. This effect will be obtained by inserting springs between the vertebrae so as to produce a force of distraction in the concavity or a compressive force in the convexity. These springs should not cause movement of the vertebrae to which they apply their forces since total correction of the deviation has already been obtained.

The measuring devices (43, 65) in distraction or in compression are put into place respectively in the concavity and in the convexity and press on the bases (5) of the corrective arms (4) of two vertebrae which are or are not adjacent. The handles (64, 76) are then rotated in the direction of the desired effect but up to the maximum value below the longitudinal movement on the rails (3) of the arms (4) to which the effect is applied. The dynamometers (54, 55, 72, 73) placed on these measuring devices (43, 65) will give us the values of the forces which must be exerted by the springs of the dynamic internal vertebral orthosis. At the same time, we see a reduction in the forces required on the rods of the orthosis, the values of these forces being still given by the dynamometers (29, 30, 40, 41) of the corrective arms (4) attached to frame (1) by their bases (5). The rods and the springs of the orthosis are then chosen in relation to these data and their insertion may be carried out.

By rotating the springs of the orthosis in torsion and locking them in relation to their points of application on the anchoring components, it will be possible to exert a certain derotating effect on the vertebrae and hence reduce accordingly the forces required on the connecting rods, the diameter of which can be reduced, the elasticity being thus increased.

In the case where osteosynthetic equipment is installed, it is not necessary to obtain a measurement of the corrective forces but it is necessary to give the means of connection the necessary shape to preserve the position of the correction obtained and then to attach this to the means of anchorage.

The operation is concluded by removing the frame (1), the corrective ends of which are detached from the means of anchorage, and the frame is then freed from its articulated arms. The incision is closed in the usual manner.

I claim:

1. A spinal operative equipment comprising:
   a frame support including longitudinal bars for extending along a spinal column,
   corrective devices slidably mounted on said longitudinal bars, each of said corrective devices comprising:
   a base for transversely attaching said corrective device to said frame while allowing free longitudinal sliding movements of said corrective devices,
   a corrective arm resting on said base and having an operational end for engagement with a corresponding side of a vertebra,
   a horizontal frontal control rod having first means for adjustment of said operational end with respect to said base in a horizontal frontal direction orthogonal to said longitudinal bars, said horizontal frontal control rod being arranged to maintain said operational end in said horizontal frontal direction after adjustment,
   a horizontal sagittal control rod having second means for adjustment of said operational end with respect to said base in a horizontal sagittal direction orthogonal to said longitudinal bars, said horizontal sagittal control rod being adapted to maintain said operational end in said horizontal sagittal direction after adjustment.

2. A spinal operative equipment as in claim 1, wherein said frame comprises two longitudinal parallel bars on either side of the spinal column and including attachment means for attaching said base to each of said bars and for allowing free longitudinal sliding movements of said base along said bars.

3. A spinal operative equipment as in claim 2, wherein said attachment means is configured so as to allow mounting or removal of each corrective device during surgery.

4. A spinal operative equipment as in claim 2, wherein said attachment means comprises,
   a cylindrical recess,
   a cylinder concentric to said cylindrical recess and enclosed in said cylindrical recess, so as to be free to rotate, and wherein said cylindrical recess and said cylinder are longitudinally open so as to allow entry of said bar in said cylinder.

5. A spinal operative equipment as in claim 1, wherein said frame support comprises four longitudinal bars, two adapted to be placed on either side of the spinal column, thus allowing mounting of one of said corrective devices and anchorage of one of said operational ends on either side of each vertebra.

6. A spinal operative equipment as in claim 1, wherein said frame support is a rectangular frame comprising two upper and lower short sides, each longitudinal side comprising two longitudinal parallel bars, said frame support being adapted to extend in a frontal plane with each of said longitudinal sides on either side of the spinal column.

7. A spinal operative equipment as in claim 1, wherein said horizontal frontal control rod comprises a manipulating handle, an axial stop engaging said corrective arm, and a thread engaging an internal thread of the base.

8. A spinal operative equipment as in claim 1, wherein said frontal control rod comprises dynamometric means adapted to measure forces exerted on said operational end along said horizontal frontal direction.

9. A spinal operative equipment as in claim 1, wherein said horizontal frontal control rod comprises means for measuring movements of said operational end along said horizontal frontal direction.

10. A spinal operative equipment as in claim 1, wherein said horizontal sagittal control rod comprises a manipulating handle, an axial stop engaging said corrective arm, and a thread engaging an internal thread of the base.

11. A spinal operative equipment as in claim 1, wherein said horizontal sagittal control rod comprises dynamometric means for measuring forces exerted on said operational end along said horizontal sagittal direction.

12. A spinal operative equipment as in claim 1, wherein said horizontal sagittal control rod comprises means for measuring movements of said operational end along said horizontal sagittal direction.

13. A spinal operative equipment as in claim 1, and including a dynamometric clamp or calliper including: (i) two dogs for engagement with holes in the bases of two distinct corrective devices, and (ii) dynamometric means for measuring forces exerted between said dogs along the vertical direction of said longitudinal bars.

14. A spinal operative equipment as in claim 13, wherein said dynamometric clamp or calliper includes means for measuring movements of said dogs along the vertical direction.

15. A spinal operative equipment as in claim 13, wherein said dynamometric clamp of calliper includes a manipulating handle, and means for adjusting and maintaining the distance between said dogs.

16. A spinal operative equipment comprising:
a frame support comprising two longitudinal side members for placement on either side of a spinal column, each longitudinal side member comprising two longitudinal parallel bars,
corrective devices slidably mounted on said longitudinal bars, each corrective device comprising:
   a base transversely attached to two longitudinal bars of one longitudinal side member by attachment means allowing free longitudinal sliding movements of said base along said bars,
   a corrective arm having an operational end engageable with a corresponding side of a vertebra, said corrective arm resting on said base,
   a horizontal frontal control rod having first means for adjustment of said operational end with respect to said base in a horizontal frontal direction orthogonal to said longitudinal bars, said horizontal frontal control rod maintaining said operational end in said horizontal frontal direction after adjustment,
   a horizontal sagittal control rod having second means for adjustment of said operational end with respect to said base in a horizontal sagittal direction orthogonal to said longitudinal bars, said horizontal sagittal control rod maintaining said operational end in said horizontal sagittal direction after adjustment.

17. A spinal operative equipment as in claim 16, wherein said attachment means allows mounting or removal of each corrective device during surgery.

18. A spinal operative equipment as in claim 16 wherein said attachment means comprises, for attachment to each of said bars
   a cylindrical recess,
   a cylinder concentric to said cylindrical recess and enclosed in said cylindrical recess, so as to be free to rotate, and wherein said cylindrical recess and said cylinder are longitudinally open so as to allow entry of said bar in said cylinder.

19. A spinal operative equipment comprising:
   a frame support including longitudinal bars adapted to extend along a spinal column of a patient,
corrective devices slidably mounted on said longitudinal bars, each corrective device comprising:
   a base adapted to transversely attach said corrective device to the frame while allowing free longitudinal sliding movements,
   a corrective arm having an operational end for engagement with a corresponding side of a vertebra, said corrective arm resting on said base,
   a horizontal frontal control rod having first means for adjustment of said operational end with respect to said base in a horizontal frontal direction orthogonal to said longitudinal bars, said horizontal frontal control rod maintaining said operational end in said horizontal frontal direction after adjustment,
   a horizontal sagittal control rod having second means for adjustment of said operational end with respect to said base in a horizontal sagittal direction orthogonal to said longitudinal bars, said horizontal sagittal control rod maintaining said operational end in said horizontal sagittal direction after adjustment,
   dynamometric means for measuring forces exerted on said operational end along said horizontal frontal direction and along said horizontal sagittal direction,
   a dynamometric clamp or calliper including: (i) two dogs for engagement in openings in two bases of two distinct corrective devices, and (ii) means adapted for measuring forces exerted between said dogs along the vertical direction of said longitudinal bars.

20. A spinal operative equipment as in claim 19, wherein said dynamometric clamp or calliper includes means for measuring movements of said dogs along the vertical direction.

21. A spinal operative equipment as in claim 19, wherein said dynamometric clamp or calliper includes a manipulating handle, and means for adjusting and maintaining the distance between said dogs.

* * * * *